(12) United States Patent
Harbeson

(10) Patent No.: US 8,198,305 B2
(45) Date of Patent: Jun. 12, 2012

(54) 1,2-BENZISOXAZOL-3-YL COMPOUNDS

(75) Inventor: Scott L. Harbeson, Cambridge, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 1002 days.

(21) Appl. No.: 12/102,164

(22) Filed: Apr. 14, 2008

(65) Prior Publication Data

US 2008/0255194 A1    Oct. 16, 2008

Related U.S. Application Data

(60) Provisional application No. 60/911,669, filed on Apr. 13, 2007.

(51) Int. Cl.
*A61K 31/454* (2006.01)
*C07D 413/04* (2006.01)

(52) U.S. Cl. ........................ 514/321; 546/198
(58) Field of Classification Search .................. 514/321; 546/198
See application file for complete search history.

(56) References Cited

U.S. PATENT DOCUMENTS

| | | | |
|---|---|---|---|
| 4,421,865 A * | 12/1983 | Shen ............................... | 521/31 |
| 5,149,820 A * | 9/1992 | Borretzen et al. ............. | 548/215 |
| 5,304,121 A | 4/1994 | Sahatjian | |
| 5,364,866 A | 11/1994 | Strupczewski et al. | |
| 5,776,963 A | 7/1998 | Strupczewski et al. | |
| 5,886,026 A | 3/1999 | Hunter et al. | |
| 6,099,562 A | 8/2000 | Ding et al. | |
| 6,100,256 A | 8/2000 | Baker et al. | |
| 6,147,072 A | 11/2000 | Bymaster et al. | |
| 6,150,355 A | 11/2000 | Kumazawa et al. | |
| 6,166,008 A | 12/2000 | Johnson et al. | |
| 6,174,886 B1 | 1/2001 | Pineiro et al. | |
| 6,221,335 B1 | 4/2001 | Foster | |
| 6,229,875 B1 | 5/2001 | Keesmaat | |
| 6,358,944 B1 | 3/2002 | Lederman et al. | |
| 6,372,919 B1 | 4/2002 | Lippa et al. | |
| 6,384,077 B1 | 5/2002 | Peet et al. | |
| 6,420,369 B1 | 7/2002 | Marcotte | |
| 6,440,710 B1 | 8/2002 | Keinan et al. | |
| 6,444,665 B1 | 9/2002 | Helton et al. | |
| 6,495,154 B1 | 12/2002 | Tam et al. | |
| 6,566,389 B1 | 5/2003 | Zisapel et al. | |
| 6,603,008 B1 | 8/2003 | Ando et al. | |
| 6,620,819 B2 | 9/2003 | Marcotte | |
| 6,667,297 B2 | 12/2003 | Tsai et al. | |
| 6,680,310 B2 | 1/2004 | Belanoff et al. | |
| 6,689,812 B2 | 2/2004 | Peet et al. | |
| 6,803,031 B2 | 10/2004 | Rabinowitz et al. | |
| 6,964,962 B2 | 11/2005 | Wong et al. | |
| 7,517,990 B2 | 4/2009 | Ito et al. | |
| 7,977,356 B2 * | 7/2011 | Grimler et al. ................ | 514/321 |
| 2006/0079502 A1 | 4/2006 | Lang | |
| 2006/0094744 A1 | 5/2006 | Maryanoff et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| EP | 0 402 644 | 8/1995 |
| WO | WO 03/20707 | 3/2003 |
| WO | WO 2004/006886 | 1/2004 |
| WO | WO 2006/039663 | 4/2006 |
| WO | WO 2007/118651 | 10/2007 |
| WO | WO 2008/099020 | 8/2008 |

OTHER PUBLICATIONS

Mutlib et al. "Application of liquid . . . " J. Pharm. Exp. The. 286(3) p. 1285-93 (1998).*
Wade "Deuterium isotope effects . . . " Chemico-giological interactions 117, p. 191-217 (1999).*
Strupczewski et al. "Preparation of . . . " CA120:54553 (1994).*
Mutlib. et al. "Application of hyphenated . . . " CA123:305855 (1995).*
Grimler et al. "Preparation of . . . " CA138:238170 (2003).*
Freireich et al., "Quantitative comparison of toxicity of anticancer agents in mouse, rat, hamster, dog, monkey, and man," *Cancer Chemother. Rep*, 1966, 50:219-244.
Gannes et al., "Natural Abundance Variations in Stable Isotopes and their Potential Uses in Animal Physiological Ecology," *Comp. Biochem. Physiol. Mol. Integr. Physiol.*, 1998, 119:725-737.
Houston, "Utility of in vitro drug metabolism data in predicting in vivo metabolic clearance," *Biochem. Pharmacol.*, 1994, 47:1469-1479.
Houston et al., "Prediction of hepatic clearance from microsomes, hepatocytes, and liver slices," *Drug Metab. Rev.*, 1997, 29:891-922.
Iwatsubo et al., "Prediction of in vivo drug metabolism in the human liver from in vitro metabolism data," *Pharmacol. Ther.*, 1997, 73:147-171.
Lave et al., "The use of human hepatocytes to select compounds based on their expected hepatic extraction ratios in humans," *Pharm. Res.*, 1997, 14:152-155.
Markey et al., "General Methods for the Synthesis of Methyl Isotope Labelled Catecholamine Metabolites. Preparation of 4-Hydroxy-3-Methoxy-$d_3$-(Mandelic Acid, Phenylacetic Acid, and Phenylethylene Glycol)," *J. Label Comp. Radiopharm.*, 1980, 17:103-114.
Mutlib et al., "Application of liquid chromatography/mass spectrometry in accelerating the identification of human liver cytochrome P450 isoforms involved in the metabolism of iloperidone," *J. Pharmacol. Exp. Ther.*, 1998, 286:1285-1293.
Obach, "Prediction of human clearance of twenty-nine drugs from hepatic microsomal intrinsic clearance data: An examination of in vitro half-life approach and nonspecific binding to microsomes," *Drug Metab. Disp.*, 1999, 27:1350-1359.
Scientific Tables, 1970, Geigy Pharmaceuticals, Ardsley, N.Y., p. 537.

(Continued)

*Primary Examiner* — Celia Chang
(74) *Attorney, Agent, or Firm* — Fish & Richardson P.C.

(57) ABSTRACT

This invention relates to novel 1,2-benzisoxazol-3-yl compounds, their derivatives, pharmaceutically acceptable salts, solvates, and hydrates thereof. This invention also provides compositions comprising a compound of this invention and the use of such compositions in methods of treating diseases and conditions that are beneficially treated by administering an antagonist of both dopamine and serotonin receptors.

9 Claims, No Drawings

OTHER PUBLICATIONS

Sharma et al., "An Effective System to Synthesize Hypolipidemic Active α-Asarone and Related Methoxylated (E)-Arylalkenes," *Bull. Chem. Soc. Jap.*, 2004, 77:2231-2235.

Strupczewski et al., "3-[[(Aryloxy)alkyl]piperidinyl]-1,2-benzisoxazoles as D2/5-HT2 antagonists with potential atypical antipsychotic activity: antipsychotic profile of iloperidone (HP 873)," *J. Med. Chem.*, 1995, 38:1119-1131.

Vanda Pharmaceuticals Press Release, Dec. 7, 2006.

Wada et al., "[Natural abundance of carbon, nitrogen, and hydrogen isotope ratios in biogenic substances: present and future]," *Seikagaku*, 1994, 66:15-29.

Yoshihara et al., "Conversion of Alcohols to Alkyl Halides using Iminium Salts," *Synthesis*, 1980, 9:746-748.

Foster, "Deuterium Isotope Effects in the Metabolism of Drugs and Xenobiotics: Implications for Drug Design," *Adv. Drug Res.*, 1985, 14:2-40.

Foster, "Deuterium isotope effects in studies of drug metabolism," *Trends in Pharmaceutical Sciences*, 1984, pp. 524-527.

Dyck et al., "Effects of Deuterium Substitution on the Catabolism of β-Phenylethylamine: An In Vivo Study," *J. Neurochem.*, 1986, 46:399-404.

Tonn et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes," *Biol. Mass Spectrometry*, 1993, 22:633-642.

Haskins, "The Application of Stable Isotopes in Biomedical Research," *Biomed. Mass Spectrometry*, 1982, 9(7):269-277.

Wolen, "The Application of Stable Isotopes to Studies of Drug Bioavailability and Bioequivalence," *J. Clin. Pharmacol.*, 1986, 26:419-424.

Browne, "Stable Isotope Techniques in Early Drug Development: An Economic Evaluation," *J. Clin. Pharmacol.*, 1998, 38:213-220.

Baillie, "The Use of Stable Isotopes in Pharmacological Research," *Pharmacol. Rev.*, 1981, 33(2):81-132.

Gouyette, "Synthesis of Deuterium-labelled Elliptinium and its Use in metabolic Studies," *Biomed Environ Mass Spectrometry*, 1988, 15:243-247.

Cherrah et al., "Study of Deuterium Isotope Effects on Protein Binding by Gas Chromatography/Mass Spectrometry. Caffeine and Deuterated Isotopomers," *Biomed Environ Mass Spectrometry*, 1987, 14:653-657.

Pieniaszek et al., "Moricizine Bioavailability via Simultaneous, Dual, Stable Isotope Administration: Bioequivalence Implications," *J. Clin. Pharmacol.*, 1999, 39:817-825.

Honma et al., "The Metabolism of Roxatidine Acetate Hydrochloride. Liberation of Deuterium from the Piperidine Ring during Hydroxylation," *Drug Metab. Dispos.*, 1987, 15(4):551-559.

Mutlib et al., "Application of Hyphenated LC/NMR and LC/MS Techniques in Rapid Identification of In Vitro and In Vivo Metabolites of Iloperidone," *Drug Metab. Dispos.*, 1995, 23(9):951-964.

Subramanian and Kalkman, "Receptor profile of P88-8991 and P95-12113, metabolites of the novel antipsychotic iloperidone," *Progress in Neuro-Psychopharmacology & Biological Psychiatry*, 2002, 26:553-560.

"Patient Information: FANAPT™ (iloperidone)," Jul. 2009, Vanda Pharmaceuticals, 18 pages.

Fisher et al., "The Complexities Inherent in Attempts to Decrease Drug Clearance by Blocking Sites of CYP-mediated Metabolism," *Curr. Opin. Drug Discovery Development*, 2006, 9(1):101-109.

Kushner et al., "Pharmacological Uses and Perspectives of Heavy Water and Deuterated Compounds," *Can. J. Pharmacol.*, 1999, 77:79-88.

Authorized Officer Ellen Moyse, International Preliminary Report on Patentability in PCT/US2008/060210 mailed Oct. 22, 2009, 7 pages.

Authorized officer Lee W. Young, International Search Report/Written Opinion in PCT/US10/27990 mailed Mar. 19, 2010, 11 pages.

Kuroboshi M. et al., "Synthesis of Perfluoroalkyl-substituted Arenes by Oxidative Desulfurization-fluroination," *J. Fluorine Chemistry*, vol. 69:127-128 (1994).

Ie, Y. et al., "Synthesis, Properties, and Structures of Difluoromethylene-bridged Coplanar *p*-Terphenyl and Its Aryl-capped Derivatives for Electronic-transporting Materials," *Chemistry Letters*, vol. 36(11):1326-1327 (2007).

\* cited by examiner

1,2-BENZISOXAZOL-3-YL COMPOUNDS

CROSS-REFERENCE TO RELATED APPLICATION

This application claims priority under 35 U.S.C. §119 to U.S. Provisional Application Ser. No. 60/911,669, filed Apr. 13, 2007, the entire contents of which are incorporated by reference herein.

This invention relates to novel 1,2-benzisoxazol-3-yl compounds, their derivatives, pharmaceutically acceptable salts, solvates, and hydrates. This invention also provides compositions comprising a compound of this invention and the use of such compositions in methods of treating diseases and conditions that are beneficially treated by administering an antagonist of both dopamine and serotonin receptors.

Iloperidone is an antipsychotic, serotonin/dopamine receptor antagonist. Iloperidone is also known as Fiapta® and Zomaril®, and by the chemical names 1-[4-[3-[4-(6-fluoro-1,2-benzisoxazol-3-yl)piperidin-1-yl]propoxy]-3-methoxyphenyl]ethanone; 1-[3-(4-acetyl-2-methoxyphenoxy)propyl]-4-(6-fluoro-1,2-benzisoxazol-3-yl)piperidine; and 4'-[3-[4-(6-fluoro-1,2-benzisoxazol-3-yl)piperidin-1-yl]propoxy]-3'-methoxyacetophenone. It is pre-registered with the FDA for the treatment of schizophrenia following a phase III clinical trial and is currently being tested for safety and efficacy in patients with an acute exacerbation of the disease. It is also in phase I clinical trials for bipolar disorder.

The reduced metabolite of iloperidone, known by the chemical names 4-[3-[4-(6-fluoro-1,2-benzisoxazol-3-yl)piperidin-1-yl]propoxy]-3-methoxy-α-methylbenzene methanol and 1-(4-(3-(4-(6-fluorobenzo[d]isoxazol-3-yl)piperidin-1-yl)propoxy)-3-methoxyphenyl)ethanol, also has serotonin/dopamine receptor antagonist activity. See, Mutlib A E et al, J Pharmacol Exp Ther 1998, 286:1285 and PCT publication WO 03/020707.

Iloperidone demonstrated variable clinical effect resulting from the level of CYP2D6 activity in patients receiving the drug. This is of concern because iloperidone is known to prolong a subject's QTc interval. For example, in patients with low CYP2D6 activity, a given dose of iloperidone can result in much higher exposure than intended and thus result in QTc prolongation. See WO 06/039663. Prolonged QTc intervals are associated with an increased risk of developing ventricular arrhythmias and can result in sudden death. In a phase III clinical trial for iloperidone, it was found that the QTc prolongation in good metabolizers of iloperidone was shorter (10.4 msec) than in poor metabolizers (15.0 msec). See *Vanda Pharmaceuticals Press Release*, Dec. 7, 2006.

Common side effects of iloperidone include nausea, anxiety, dizziness, insomnia, low blood pressure, muscle stiffness, muscle pain, sedation, tremors, increased salivation, and weight gain (e.g., gains of greater than 50 pounds). These compounds have also been known to cause sexual dysfunction (e.g., retrograde ejaculation). Additionally, breast tenderness and lactation (in both genders) may occur. Many antipsychotics are known to increase prolactin because they inhibit dopamine. Thus, iloperidone can potentially cause tardive dyskinesia (TD), extrapyramidal symptoms (EPS), and neuroleptic malignant syndrome (NMS).

Despite the beneficial activities of iloperidone, there is a continuing need for new compounds to treat the aforementioned diseases and conditions.

DEFINITIONS

The terms "ameliorate" and "treat" are used interchangeably and include therapeutic and/or prophylactic treatment. Both terms mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

The term "QTc," as used herein, means the time between the start of the Q wave and the end of the T wave in the heart's electrical cycle, corrected for the subject's heart rate.

In the compounds of this invention any atom not specifically designated as a particular isotope is meant to represent any stable isotope of that atom unless otherwise stated. Unless otherwise stated, when a position is designated specifically as "H" or "hydrogen", the position is understood to have hydrogen at its natural abundance isotopic composition.

It will be recognized that some variation of natural isotopic abundance occurs in a synthesized compound depending upon the origin of chemical materials used in the synthesis. Thus, a preparation of a particular compound will inherently contain small amounts of deuterated and/or $^{13}$C-containing isotopologues. The concentration of such naturally abundant stable hydrogen and carbon isotopes, notwithstanding this variation, is small and immaterial as compared to the degree of stable isotopic substitution of compounds of this invention. See, for instance, Wada E et al, Seikagaku 1994, 66:15; Ganes L Z et al., Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. Positions designated as having deuterium typically have a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that has the same chemical structure and formula as a specific compound of this invention, with the exception of the isotopic composition at one or more positions, e.g., H vs. D. Thus an isotopologue differs from a specific compound of this invention in the isotopic composition thereof.

The term "compound," as used herein, is also intended to include any salts, solvates, or hydrates thereof.

A salt of a compound of this invention is formed between an acid and a basic group of the compound, such as an amino functional group, or a base and an acidic group of the compound, such as a carboxyl functional group. Accordingly, in one embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as, e.g., water, acetone, ethanol, methanol, dichloromethane, 2-propanol, or the like, bound by non-covalent intermolecular forces.

The compounds of the present invention (e.g., compounds of Formula I), may contain one or more stereogenic centers. Accordingly, compounds of this invention can exist as either individual stereoisomers or mixtures of two or more stereoisomers. A compound of the present invention will include both mixtures (e.g., racemic mixtures) and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolable or storable intermediate compounds, treating a disease or condition responsive to therapeutic agents).

The term "stereoisomer" refers to a molecule capable of existing in more than one spatial atomic arrangement for a given atomic connectivity (e.g., enantiomers, meso compounds, and diastereomers). As used herein, the term "stereoisomer" means either or both enantiomers and diastereomers.

"D" refers to deuterium.

"Stereoisomer" refers to both enantiomers and diastereomers.

"Tert", "t", and "t-" each refer to tertiary.

"US" refers to the United States of America.

"FDA" refers to Food and Drug Administration.

Throughout this specification, reference to "each R" includes, independently, any "R" group (e.g., $R^{1a}$, $R^{1b}$, $R^2$, $R^{3a}$, $R^{3b}$, etc.) where applicable.

Therapeutic Compounds

The present invention provides an isolated compound of Formula I, which includes salts, hydrates, and solvates thereof,

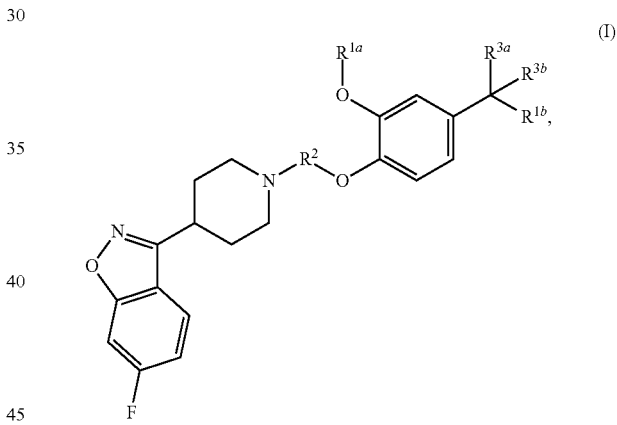

wherein:

$R^{1a}$ and $R^{1b}$ are each independently selected from —$CH_3$, —$CH_2D$, -$CHD_2$, and -$CD_3$;

$R^2$ is —$CH_nD_{(2-n)}CH_mD_{(2-m)}CH_pD_{(2-p)}$-, wherein each of n, m, and p is independently selected from 0, 1, and 2 ($R^2$ may also be referred to as an n-propylene wherein 1 to 6 hydrogen atoms are optionally replaced by deuterium);

$R^{3a}$ is selected from H, D, and F;

$R^{3b}$ is selected from H, D, and F, and, when $R^{3a}$ is H or D, $R^{3b}$ is additionally selected from —OH; or $R^{3a}$ and $R^{3b}$ are taken together, with the carbon atom to which they are bound, to form a carbonyl group; or $R^{3a}$ and $R^{3b}$ are taken together, with the carbon atom to which they are bound, to form a cyclopropyl ring; and at least one R group (i.e., $R^{1a}$, $R^{1b}$, $R^2$, $R^{3a}$, and $R^{3b}$) comprises a deuterium atom.

The present invention provides a compound of Formula I, which includes salts, hydrates, and solvates thereof,

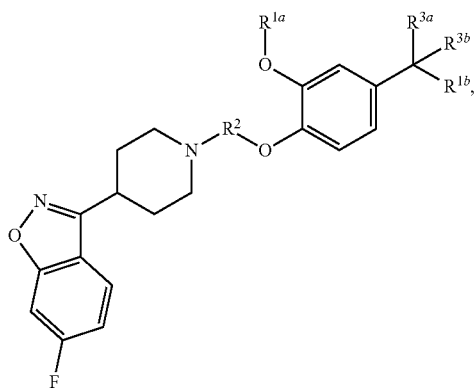

(I)

wherein:

$R^{1a}$ and $R^{1b}$ are each independently selected from —$CH_3$, —$CH_2D$, -$CHD_2$, and -$CD_3$;

$R^2$ is —$CH_nD_{(2-n)}CH_mD_{(2-m)}CH_pD_{(2-p)}$-, wherein each of n, m, and p is independently selected from 0, 1, and 2 ($R^2$ may also be referred to as an n-propylene wherein 1 to 6 hydrogen atoms are optionally replaced by deuterium);

$R^{3a}$ is selected from H, D, and F;

$R^{3b}$ is selected from H, D, and F, and, when $R^{3a}$ is H or D, $R^{3b}$ is additionally selected from —OH; or $R^{3a}$ and $R^{3b}$ are taken together, with the carbon atom to which they are bound, to form a carbonyl group; or $R^{3a}$ and $R^{3b}$ are taken together, with the carbon atom to which they are bound, to form a cyclopropyl ring; and at least one R group (i.e., $R^{1a}$, $R^{1b}$, $R^2$, $R^{3a}$, and $R^{3b}$) comprises a deuterium atom.

For the avoidance of doubt, the orientation of $R^2$ in a compound of Formula I is such that the $CH_nD_{(2-n)}$ methylene unit (or the left-most indicated methylene unit) is bound to the piperidinyl nitrogen.

In one embodiment, each of $R^{1a}$ and $R^{1b}$ is independently selected from $CH_3$ and $CD_3$.

In another embodiment, $R^{1a}$ and $R^{1b}$ are simultaneously $CD_3$.

In still another embodiment $R^{1a}$ is $CD_3$ and $R^{1b}$ is $CH_3$.

In another embodiment, each of n, m and p is independently selected from 0 and 2. In other words, $R^2$ is selected from $CH_2CH_2CH_2$, $CH_2CH_2CD_2$, $CH_2CD_2CD_2$, $CH_2CD_2CH_2$, $CD_2CD_2CD_2$, $CD_2CD_2CH_2$, $CD_2CH_2CD_2$, and $CD_2CH_2CH_2$.

In certain embodiments, m is 2, one of n or p is 2, and the other of n or p is 0 or 2. In other words, $R^2$ is selected from $CH_2CH_2CH_2$, $CH_2CH_2CD_2$, and $CD_2CH_2CH_2$.

In other embodiments, m is 0 and each of n and p is independently selected from 0 and 2. In other words, $R^2$ is selected from $CH_2CD_2CD_2$, $CH_2CD_2CH_2$, $CD_2CD_2CD_2$, and $CD_2CD_2CH_2$, In still other embodiments, $R^{3a}$ is hydrogen and $R^{3b}$ is selected from —OH and F.

In another embodiment, $R^{3a}$ and $R^{3b}$ are taken together, with the carbon atom to which they are bound, to form a carbonyl group.

In still other embodiments, $R^{3a}$ and $R^{3b}$ are simultaneously D.

In still other embodiments, $R^{3a}$ and $R^{3b}$ are simultaneously F.

In another embodiment, the compound is any one of the compounds set forth in Table 1:

TABLE 1

Exemplary Embodiments of Formula I

| Cmpd | $R^{1a}$ | $R^{1b}$ | $R^2$ | $R^{3a}$ | $R^{3b}$ |
|---|---|---|---|---|---|
| 100 | $CH_3$ | $CH_3$ | $CD_2CH_2CH_2$ | H | OH |
| 101 | $CD_3$ | $CH_3$ | $CD_2CH_2CH_2$ | H | OH |
| 102 | $CH_3$ | $CD_3$ | $CD_2CH_2CH_2$ | H | OH |
| 103 | $CH_3$ | $CH_3$ | $CD_2CH_2CD_2$ | H | OH |
| 104 | $CD_3$ | $CH_3$ | $CD_2CH_2CD_2$ | H | OH |
| 105 | $CH_3$ | $CD_3$ | $CD_2CH_2CD_2$ | H | OH |
| 106 | $CD_3$ | $CD_3$ | $CD_2CH_2CH_2$ | H | OH |
| 107 | $CD_3$ | $CD_3$ | $CD_2CH_2CD_2$ | H | OH |
| 108 | $CH_3$ | $CH_3$ | $CD_2CH_2CH_2$ | H | F |
| 109 | $CD_3$ | $CH_3$ | $CD_2CH_2CH_2$ | H | F |
| 110 | $CH_3$ | $CD_3$ | $CD_2CH_2CH_2$ | H | F |
| 111 | $CH_3$ | $CH_3$ | $CD_2CH_2CD_2$ | H | F |
| 112 | $CD_3$ | $CH_3$ | $CD_2CH_2CD_2$ | H | F |
| 113 | $CH_3$ | $CD_3$ | $CD_2CH_2CD_2$ | H | F |
| 114 | $CD_3$ | $CD_3$ | $CD_2CH_2CH_2$ | H | F |
| 115 | $CD_3$ | $CD_3$ | $CD_2CH_2CD_2$ | H | F |
| 116 | $CH_3$ | $CH_3$ | $CD_2CH_2CH_2$ | F | F |
| 117 | $CH_3$ | $CH_3$ | $CD_2CH_2CD_2$ | F | F |
| 118 | $CD_3$ | $CH_3$ | $CD_2CH_2CH_2$ | F | F |
| 119 | $CH_3$ | $CD_3$ | $CD_2CH_2CH_2$ | F | F |
| 120 | $CD_3$ | $CH_3$ | $CD_2CH_2CD_2$ | F | F |
| 121 | $CH_3$ | $CD_3$ | $CD_2CH_2CD_2$ | F | F |
| 122 | $CD_3$ | $CD_3$ | $CD_2CH_2CD_2$ | F | F |
| 123 | $CH_3$ | $CH_3$ | $CD_2CH_2CH_2$ | cyclopropyl | |
| 124 | $CH_3$ | $CH_3$ | $CD_2CH_2CD_2$ | cyclopropyl | |
| 125 | $CD_3$ | $CH_3$ | $CD_2CH_2CH_2$ | cyclopropyl | |
| 126 | $CH_3$ | $CD_3$ | $CD_2CH_2CH_2$ | cyclopropyl | |
| 127 | $CD_3$ | $CH_3$ | $CD_2CH_2CD_2$ | cyclopropyl | |
| 128 | $CH_3$ | $CD_3$ | $CD_2CH_2CD_2$ | cyclopropyl | |
| 129 | $CD_3$ | $CD_3$ | $CD_2CH_2CD_2$ | cyclopropyl | |
| 130 | $CH_3$ | $CD_3$ | $CH_2CH_2CH_2$ | =O | |
| 131 | $CD_3$ | $CH_3$ | $CH_2CH_2CH_2$ | =O | |
| 132 | $CD_3$ | $CD_3$ | $CH_2CH_2CH_2$ | =O | |
| 133 | $CH_3$ | $CH_3$ | $CD_2CH_2CH_2$ | =O | |
| 134 | $CD_3$ | $CH_3$ | $CD_2CH_2CH_2$ | =O | |
| 135 | $CH_3$ | $CD_3$ | $CD_2CH_2CH_2$ | =O | |
| 136 | $CD_3$ | $CD_3$ | $CD_2CH_2CH_2$ | =O | |
| 137 | $CH_3$ | $CH_3$ | $CD_2CH_2CD_2$ | =O | |
| 138 | $CD_3$ | $CH_3$ | $CD_2CH_2CD_2$ | =O | |
| 139 | $CH_3$ | $CD_3$ | $CD_2CH_2CD_2$ | =O | |
| 140 | $CD_3$ | $CD_3$ | $CD_2CH_2CD_2$ | =O | |
| 141 | $CD_3$ | $CD_3$ | $CD_2CD_2CD_2$ | =O | |
| 142 | $CD_3$ | $CH_3$ | $CD_2CD_2CD_2$ | F | F |
| 143 | $CD_3$ | $CH_3$ | $CH_2CH_2CH_2$ | F | F |

In a more specific embodiment, the compound of Formula I is selected from:

Compound 131

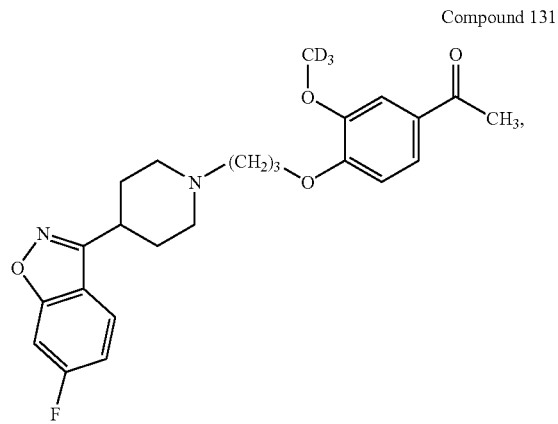

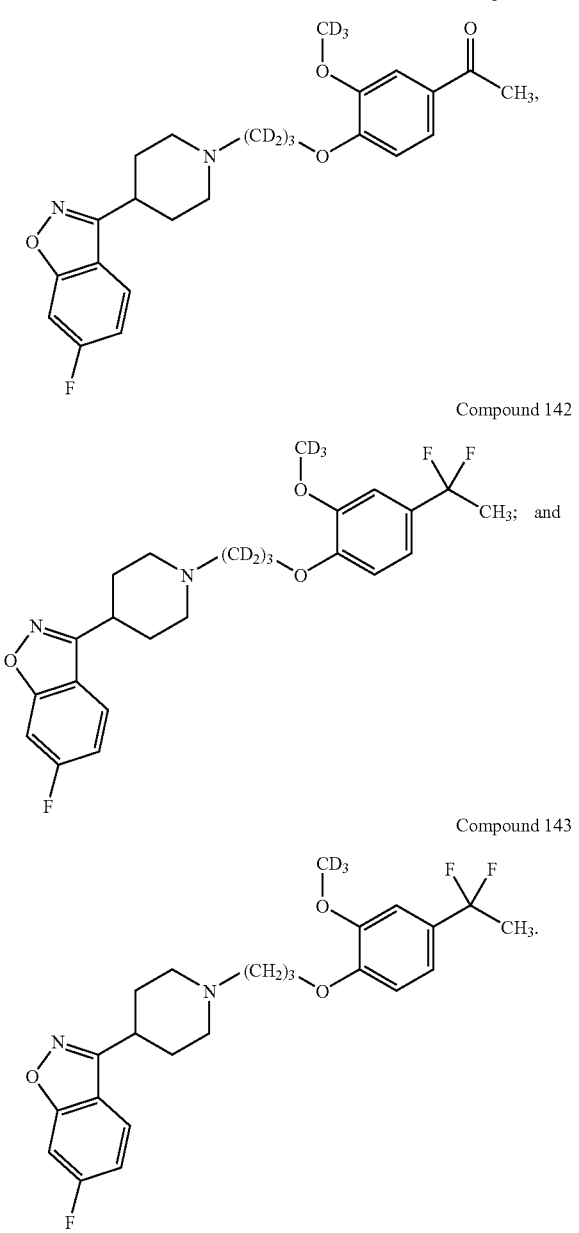

Compound 141

Compound 142

Compound 143

In another specific set of embodiments, each atom not specified as deuterium in any of the compounds of the foregoing embodiments is present at its natural isotopic abundance.

In another set of embodiments, the compound of Formula I is isolated or purified, e.g., the compound of Formula I is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues of Formula I present. Thus, in some embodiments, a composition comprising a compound of Formula I can include a distribution of isotopologues of the compound, provided at least 50% of the isotopologues by weight are the recited compound.

In some embodiments, any position in the compound of Formula I designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula I. Thus, in some embodiments, a composition comprising a compound of Formula I can include a distribution of isotopologues of the compound, provided at least 45% of the isotopologues include a D at the designated position(s).

In some embodiments, a compound of Formula I is "substantially free of" other isotopologues of the compound, e.g., less than 50%, less than 25%, less than 10%, less than 5%, less than 2%, less than 1%, or less than 0.5% of other isotopologues are present.

Exemplary Syntheses

The synthesis of compounds of Formula I can be readily achieved by synthetic chemists of ordinary skill. Relevant procedures and intermediates are disclosed, for instance in EP 0402644; Matlib, E A et al, J Pharm Exper Ther 1998, 286(3): 1285; and Strupczewski, J T et al, J Ed Chem 1995, 38:1119.

Such methods can be carried out utilizing corresponding deuterated and optionally, other isotope-containing reagents and/or intermediates to synthesize the compounds delineated herein or by invoking standard synthetic protocols known in the art for introducing isotopic atoms to a chemical structure.

One generally applicable synthesis for preparing compounds of Formula I involves coupling together two starting materials via a substitution reaction, as depicted in Scheme 1.

Scheme 1: Exemplary Synthesis of Compounds of Formula I

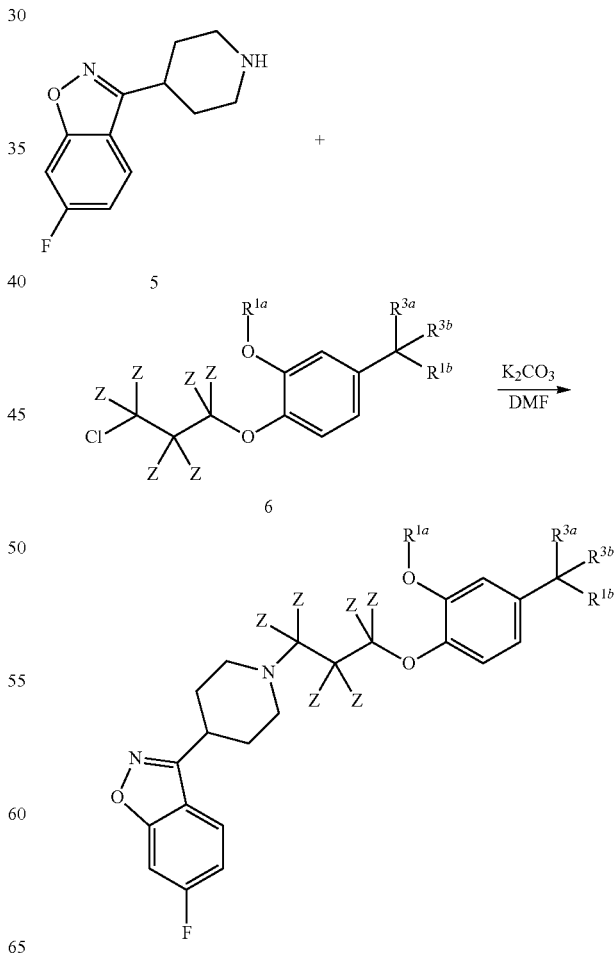

Formula I

Scheme 1 illustrates that the compounds of Formula I can be readily prepared by a substitution reaction in which a piperidinyl compound (5) displaces a chloride leaving group on an appropriately deuterated 4-(3-chloropropoxy)-3-methoxyphenyl intermediate (6). The groups $R^{1a}$, $R^{1b}$, $R^{3a}$, and $R^{3b}$ are as defined above in Formula I. The optionally-deuterated bridging propyl group ($R^2$) in Formula I is represented structurally in Scheme 1, and each Z is independently hydrogen or deuterium. In one synthetic strategy, intermediate (6) comprises the sites of optional deuteration that may ultimately be incorporated into the compounds of Formula I.

Scheme 2 illustrates exemplary syntheses of a deuterated intermediate, such as intermediate (14) or intermediate (17), either of which may subsequently be utilized in place of intermediate (6) in Scheme 1, to provide compounds of Formula I.

Scheme 2: Synthetic Routes to Intermediates 14 and 17

Alternatively, (13) can be alkylated with methyl 3-bromopropionate under analogous conditions to provide (15). The alcohol group of (15) may be protected (for instance, by addition of a protecting group (PG) via procedures well known in the chemical art), thereafter enabling the subsequent reduction of the ester with lithium aluminum deuteride to provide (16). The primary alcohol moiety in (16) can be converted to a chloride by the methods described by Yoshihara, M et al, Synthesis 1980, 9: 746, followed by deprotection of the secondary alcohol to provide (17). Like (14), intermediate (17) can undergo a substitution reaction with Compound 5, as shown in Scheme 1, in order to provide a compound of Formula I.

Scheme 3: Alternate Approach to the Synthesis of Compounds of the Structure of Intermediate 6

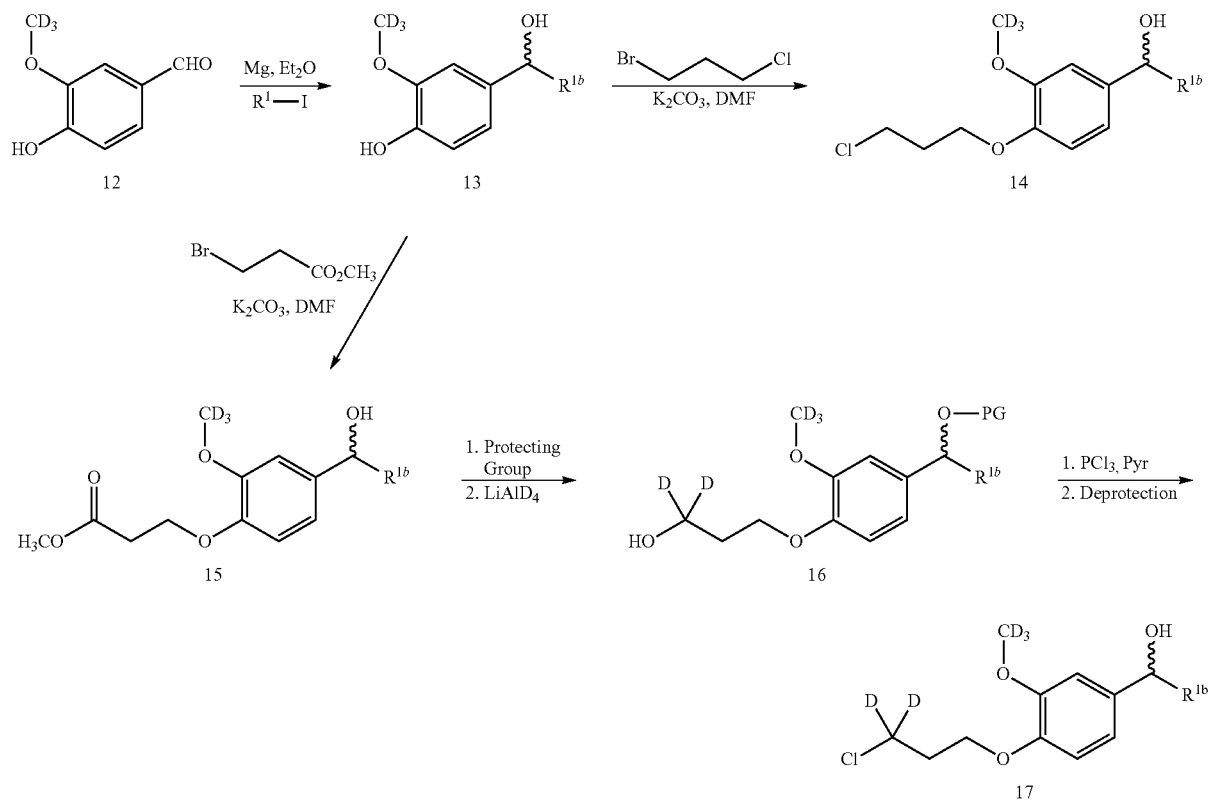

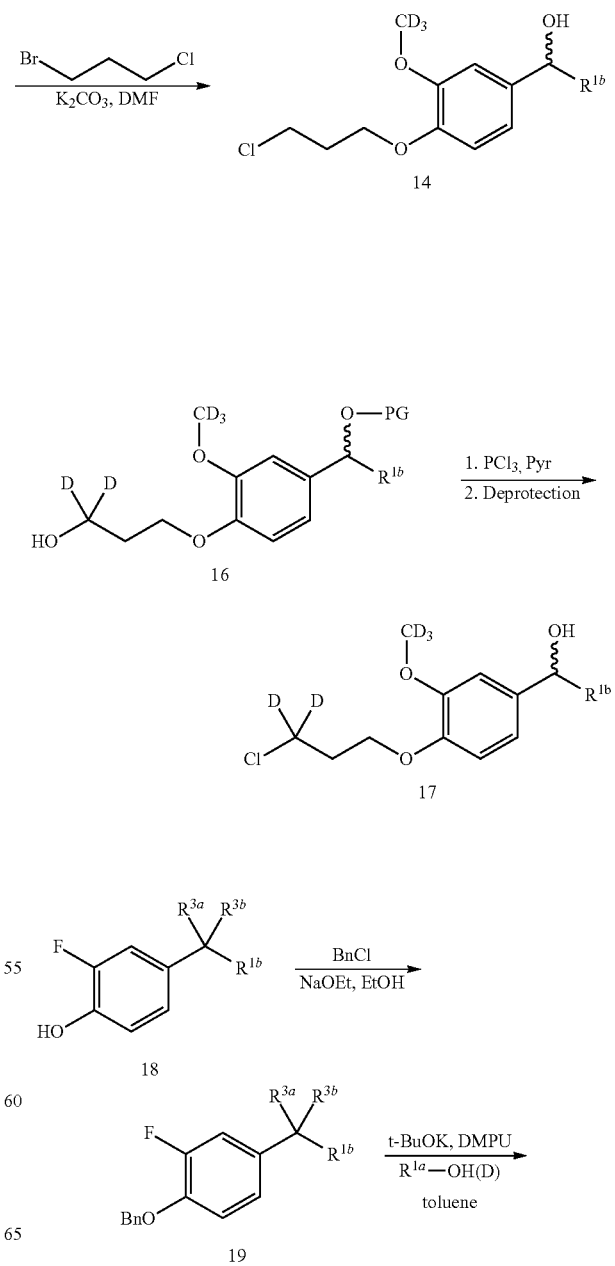

Starting material (12), which may be prepared as described by Markey S P et al, J Label Comp Radiopharm 1980, 17:103, can be reacted with the Grignard reagent derived from iodomethane (i.e., $R^{1b}=CH_3$) or iodomethane-$d_3$ (i.e., $R^{1b}=CD_3$) to provide (13). See Sharma A et al, Bull Chem Soc Jap 2004, 77: 2231. As illustrated, this reaction provides a mixture of enantiomers. If desired, this mixture can be resolved to afford stereoisomerically pure (13) or, alternatively, any subsequent product derived from (13) may be resolved using techniques well known in the chemical arts. Compound (13) can then be alkylated with 3-chloropropyl bromide, under basic conditions (e.g., potassium carbonate in DMF), to yield (14). See Strupczewski, J T et al, J Med Chem 1995, 38: 1119. Intermediate (14) can then be used in place of (6) in the substitution reaction illustrated in Scheme 1.

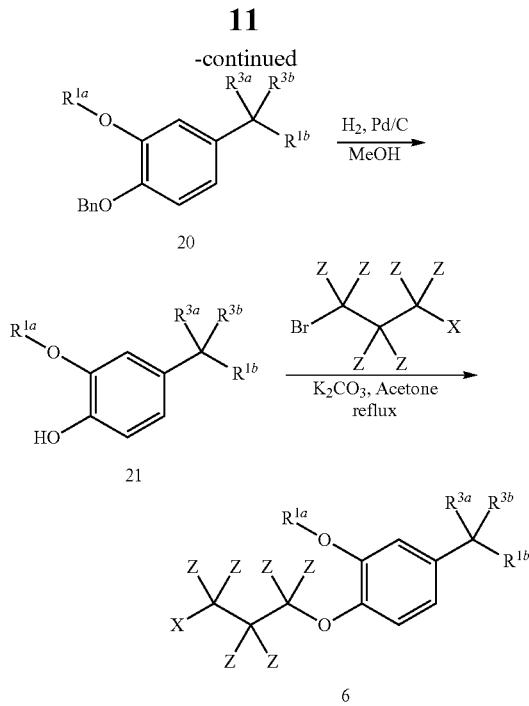

Compounds of the general formula of intermediate 6 (see Scheme 1) may be synthesized as illustrated in Scheme 3 as an alternate approach to that depicted in Scheme 2. Protection of the alcohol moiety of fluoro-phenol 18 can be carried out using benzyl chloride in the presence of a base such as NaOEt to yield benzyl ether 19. Conversion of the fluoro group in 19 to the $R^{1a}$-alkoxy moiety can be effected using $R^{1a}OH(D)$ in the presence of a base such as t-BuOK and DMPU. Deprotection of the resulting ether 20 under typical hydrogenation conditions affords the alcohol 21, which can then be alkylated with an appropriately deuterated 3-halopropylbromide to provide compounds of the general formula of intermediate 6 under conditions analogous to those used to provide intermediates 14 and 15 (see Scheme 2).

The specific approaches and compounds shown above are not intended to be limiting. The chemical structures in the schemes above depict variables that are defined commensurately with chemical group definitions of the corresponding position in the compound of Formula I, whether identified by the same variable name (e.g., $R^1$, $R^2$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, Ed., *Encyclopedia of Reagents for Organic Synthesis*, John Wiley and Sons (1995) and subsequent editions thereof.

Compositions

The invention also provides pyrogen-free compositions comprising an effective amount of a compound of Formula I or a pharmaceutically acceptable salt, solvate, or hydrate thereof, and an acceptable carrier. In one embodiment, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, e.g., *Remington's Pharmaceutical Sciences*, Mack Publishing Company, Philadelphia, Pa., 17th Ed. (1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible (e.g., because of removal from the patient or surgical procedure) such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound known to antagonize either or both dopamine and serotonin receptors. Such agents include but are not limited to those described as being useful in combination with iloperidone, risperidone, palperidone or agents of the same chemical class, such as disclosed in U.S. Pat. Nos. 5,364,866; 5,776,963, 6,100,256; 6,147,072; 6,150,355; 6,166,008; 6,174,886; 6,229,875; 6,667,297; 6,358,944; 6,372,919; 6,384,077; 6,689,812; 6,420,369; 6,620,819; 6,444,665; 6,495,154; 6,566,389; 6,680,310; and 6,964,962.

In another embodiment, the second therapeutic agent is an agent useful in the treatment or prevention of a disease or condition selected from the following diseases and conditions: affective psychosis aggression; Alzheimer disease; Alzheimer type dementia; Alzheimer type senile dementia; amphetamine dependence (e.g., methamphetamine dependence); anorexia nervosa; anxiety disorder; Asperger's disorder; bipolar disorders ((e.g., bipolar I disorder, bipolar mania, and bipolar depression)); child development disorders; cocaine dependence; conduct disorder; dementia with agitation; diabetes (e.g., type 2 diabetes mellitus); hyperglycemia; hyperprolactinemia; insulin resistance; major depressive disorders (e.g., major depressive disorder with panic attacks, major depressive disorder with suicidality) mania; metabolic syndromes (e.g., metabolic syndrome X); mood disorders; obsessive-compulsive disorder; panic disorder; post-traumatic stress disorders; prodromal schizophrenia; psychosis; psychotic disorders (e.g., psychotic disorder NOS); schizoaffective disorder; schizophrenia; schizophreniform disorder; and substance abuse (e.g., marijuana abuse and alcohol abuse).

In another embodiment, the second therapeutic agent is selected from lithium, valproate, carbamazepine, haloperidol, ADP-103, clozapine, bromocriptine, olanzapine, quetiapine, aripiprazole, escitalopram, SB-773812, ziprasidone, valnoctamide, licarbazepine, fluoxetine, venlafaxine, citalopram, fluvoxamine, paroxetine, sertraline, milnacipran, duloxetine, amino acids and their derivatives, topiramate, acetaminophen, indomethacin, Tylenol #3, melatonin, tricyclic antidepressants, anticonvulsants, serotonin reuptake inhibitors, mixed serotonin-norepinephrine reuptake inhibitors, serotonin receptor agonists and antagonists, cholinergic analgesics, adrenergic agents, neurokinin antagonists, mifepristone, cyamemazine, and reboxetine.

In still another embodiment, the second therapeutic agent is selected from melatonin or a melatonin antagonist. In a more specific embodiment, the second therapeutic agent is selected from melatonin, (1R-Trans)-N-[[2-(2,3-dihydro-4-benzofuranyl)cyclo-propyl]methyl]propanamide, N-[1-(2,3-dihydrobenzofuran-4-yl)pyrrolidin-3-yl]-N-ethylurea], ramelteon, GR196429, LY156735, agomelatine, 2-phenylmelatonin, 8-M-PDOT, 2-iodomelatonin, 6-chloromelatonin, TAK-375, CGP 52608, GR196429, S20242, S-23478, S24268, S25150, GW-290569, and IP-101. In a still more specific embodiment, the second therapeutic agent is selected from melatonin, (1R-Trans)-N-[[2-(2,3-dihydro-4-benzofuranyl)cyclo-propyl]methyl]propanamide, N-[1-(2,3-dihydrobenzofuran-4-yl)pyrrolidin-3-yl]-N-ethylurea], ramelteon, GR196429, LY156735, agomelatine, 2-phenylmelatonin, 8-M-PDOT, 2-iodomelatonin, and 6-chloromelatonin.

In another embodiment, the compound of Formula I and one or more of any of the above-described second therapeutic agents are provided as separate dosage forms, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., Cancer Chemother. Rep. 1966, 50: 219. Body surface area may be approximately determined from height and weight of the patient. See, e.g., *Scientific Tables*, Geigy Pharmaceuticals, Ardsley, N.Y., (1970) 537.

In one embodiment, an effective amount of a compound of this invention can range from about 0.06 µg/kg to about 300 mg/kg.

In another embodiment, an effective amount of a compound of this invention can range from about 0.6 µg/kg to about 30 mg/kg.

In another embodiment, an effective amount of a compound of this invention can range from about 6 µg/kg to about 3 mg/kg.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., Eds., *Pharmacotherapy Handbook*, 2nd Ed., Appleton and Lange, Stamford, Conn. (2000); *PDR Pharmacopoeia, Tarascon Pocket Pharmacopoeia* 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of a dopamine and/or a serotonin receptor in a cell, comprising contacting the cell with one or more compounds of Formula I herein. The cell can be a cell of a mammal, e.g., human, monkey, horse, cow, rat, mouse, cat, dog, sheep, or pig.

According to another embodiment, the invention provides a method of treating a subject suffering from, or susceptible to, a disease that is beneficially treated by modulating the activity of dopamine and/or serotonin receptors in a cell, comprising the step of administering to the subject an effective amount of a compound or a composition of this invention. Such diseases are well known in the art and include, but are not limited to the following diseases and conditions: affective psychosis aggression, Alzheimer disease, Alzheimer type dementia, Alzheimer type senile dementia, amphetamine dependence (e.g., methamphetamine dependence), anorexia nervosa, anxiety disorder, Asperger's disorder, bipolar disorders (e.g., bipolar I disorder, bipolar mania, and bipolar depression), child development disorders, cocaine dependence, conduct disorder, dementia with agitation, diabetes (e.g., type 2 diabetes mellitus), hyperglycemia, hyperprolactinemia, insulin resistance, major depressive disorders (e.g., major depressive disorder with panic attacks, major depressive disorder with suicidality), mania, metabolic syndromes (e.g., metabolic syndrome X), mood disorders, obsessive-compulsive disorder, panic disorder, post-traumatic stress disorders, prodromal schizophrenia, psychosis, psychotic disorders (e.g., psychotic disorder NOS), schizoaffective disorder, schizophrenia, schizophreniform disorder, and substance abuse (e.g., marijuana abuse and alcohol abuse).

In a particular embodiment, the method of this invention is used to treat a subject suffering from or susceptible to dementia, schizophrenia or schizoaffective disorder.

In a particular embodiment, the method of this invention is used to treat a subject suffering from or susceptible to schizophrenia, depression, insomnia and psychoses.

In an even more particular embodiment, the method of this invention is used to treat a subject suffering from or susceptible to schizophrenia.

Identifying a subject in need of such treatment can be in the judgment of a subject or a health care professional and can be subjective (e.g., opinion) or objective (e.g., measurable by a test or diagnostic method).

In another embodiment, any of the above methods of treatment comprises the further step of co-administering to a patient in need thereof, one or more second therapeutic agents. The choice of second therapeutic agent may be made from any of the examples of second therapeutic agents described above for use in combination compositions. The combination therapies of this invention include co-administering a second therapeutic agent useful in treating a patient suffering from or susceptible to affective psychosis aggression, Alzheimer disease, Alzheimer type dementia, Alzheimer type senile dementia, amphetamine dependence (e.g., methamphetamine dependence), anorexia nervosa, anxiety disorder, Asperger's disorder, bipolar disorders (e.g., bipolar I disorder, bipolar mania, and bipolar depression), child development disorders, cocaine dependence, conduct disorder, dementia with agitation, diabetes (e.g., type 2 diabetes mellitus), hyperglycemia, hyperprolactinemia, insulin resistance, major depressive disorders (e.g., major depressive disorder with panic attacks, major depressive disorder with suicidality), mania, metabolic syndromes (e.g., metabolic syndrome X), mood disorders, obsessive-compulsive disorder, panic disorder, post-traumatic stress disorders, prodromal schizophrenia, psychosis, psychotic disorders (e.g., psychotic disorder NOS), schizoaffective disorder, schizophrenia, schizophreniform disorder, and substance abuse (e.g., marijuana abuse and alcohol abuse). In a particular embodiment, the combination therapies of this invention include the treatment of schizophrenia.

In a more specific embodiment, the second therapeutic agent is useful in treating a patent suffering from or susceptible to a disease or condition selected from schizophrenia, depression, insomnia and psychosis.

In another specific embodiment, the second therapeutic agent is melatonin or a melatonin agonist. In an even more specific embodiment, the second therapeutic agent is selected from melatonin, (1R-Trans)-N-[[2-(2,3-dihydro-4-benzofuranyl)cyclo-propyl]methyl]propanamide, N-[1-(2,3-dihydrobenzofuran-4-yl)pyrrolidin-3-yl]-N-ethylurea], ramelteon, GR196429, LY156735, agomelatine, 2-phenylmelatonin, 8-M-PDOT, 2-iodomelatonin, and 6-chloromelatonin; and the patient is suffering from or susceptible to insomnia or depression.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., Eds., *Pharmacotherapy Handbook*, 2nd Ed., Appleton and Lange, Stamford, Conn. (2000); *PDR Pharmacopoeia, Tarascon Pocket Pharmacopoeia* 2000, Deluxe Edition, Tarascon Publishing, Loma Linda, Calif. (2000), and other medical texts. However, it is well within the skilled artisan's purview to determine the second therapeutic agent's optimal effective-amount range.

In another embodiment, where a second therapeutic agent is administered to a subject, the effective amount of the compound of this invention is less than its effective amount would be where the second therapeutic agent is not administered. In this way, undesired side effects associated with high doses of either agent may be minimized. Other potential advantages (including without limitation improved dosing regimens and/or reduced drug cost) will be apparent to those of skill in the art.

In another embodiment, this invention provides for the use of a compound of Formula I, alone or together with one of the above-described second therapeutic agents, in the manufacture of a medicament, either in a single composition or in separate dosage forms, for treating a disease that is beneficially treated by modulating the activity of dopamine and/or serotonin receptors in a cell. Such diseases are well known in the art and are disclosed in clinical trial number NCT00254202 and include affective psychosis aggression, Alzheimer disease, Alzheimer type dementia, Alzheimer type senile dementia, amphetamine dependence (e.g., methamphetamine dependence), anorexia nervosa, anxiety disorder, Asperger's disorder, bipolar disorders (e.g., bipolar I disorder, bipolar mania, and bipolar depression), child development disorders, cocaine dependence, conduct disorder, dementia with agitation, diabetes (e.g., type 2 diabetes mellitus), hyperglycemia, hyperprolactinemia, insulin resistance, major depressive disorders (e.g., major depressive disorder with panic attacks, major depressive disorder with suicidality), mania, metabolic syndromes (e.g., metabolic syndrome X), mood disorders, obsessive-compulsive disorder, panic disorder, post-traumatic stress disorders, prodromal schizophrenia, psychosis, psychotic disorders (e.g., psychotic disorder NOS), schizoaffective disorder, schizophrenia, schizophreniform disorder, and substance abuse (e.g., marijuana abuse and alcohol abuse).

Diagnostic Methods and Kits

The compounds and compositions of this invention are also useful as reagents in methods for determining the concentration of iloperidone or the reduced metabolite of iloperidone in a solution or biological sample such as plasma, for examining the metabolism of iloperidone or the reduced metabolite of iloperidone, and for other analytical studies. Additional utility of compounds of Formula I include their use as internal standards to determine the true concentration(s) of corresponding non-deuterated compounds (e.g., iloperidone or the reduced metabolite of iloperidone) in biological matrices, such as plasma.

According to one embodiment, the invention provides a method of determining the concentration, in a solution or biological sample of iloperidone or the reduced metabolite of iloperidone corresponding to a compound of Formula I, comprising the steps of:

a) adding a known concentration of the compound of Formula I, to the solution or biological sample;

b) subjecting the solution or biological sample to a measuring device that distinguishes iloperidone or the reduced metabolite of iloperidone from a corresponding compound of Formula I;

c) calibrating the measuring device to correlate the detected quantity of the compound of Formula I with the known concentration of the compound of Formula I added to the solution or biological sample; and d) measuring the quantity of iloperidone or the reduced metabolite of iloperidone in the solution or biological sample with the calibrated measuring device; and e) determining the concentration of iloperidone or the reduced metabolite of iloperidone in the solution or biological sample using the correlation between the detected quantity and concentration of the corresponding compound of Formula I.

Measuring devices that can distinguish iloperidone or the reduced metabolite of iloperidone from a corresponding compound of Formula I include any measuring device that can distinguish between two compounds that differ from one another in isotopic abundance. Exemplary measuring devices include a mass spectrometer, NMR spectrometer, and IR spectrometer.

In another embodiment, the invention provides a method of evaluating the metabolic stability of a compound of Formula I, comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a subject following administration of the compound of Formula I. This method comprises the steps of obtaining a serum, urine, or feces sample from the subject at a period of time following the administration of the compound of Formula I to the subject and comparing the amount of the compound of Formula I with the metabolic products of the compound of Formula I in the serum, urine, or feces sample.

The present invention also provides kits for use to treat any of the diseases or disorders described previously, including, e.g., schizophrenia. These kits comprise (a) a pharmaceutical composition comprising a compound of Formula I (including a salt, hydrate, or solvate thereof), wherein the pharmaceutical composition is in a container; and (b) instructions describing a method of using the pharmaceutical composition to treat schizophrenia.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kit may additionally comprise a memory aid of the type containing information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information. For single dose dispensers, memory aids further include a mechanical counter which indicates the number of daily doses that have been dispensed and a battery-powered micro-chip memory coupled with a liquid crystal readout and/or audible reminder signal which, for example, reads out the date that the last daily dose has been taken and/or reminds one when the next dose is to be taken. Other memory aids useful in such kits are a calendar printed on a card, as well as other variations that will be readily apparent.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

EXAMPLES

Example 1

Synthesis of 1-(4-hydroxy-3-methoxy-d3-phenyl)ethanone (Intermediate 26)

Intermediate 26 was prepared as outlined in Scheme 4, below. Details of the synthesis are set forth below.

Scheme 4: Synthesis of Intermediate 26

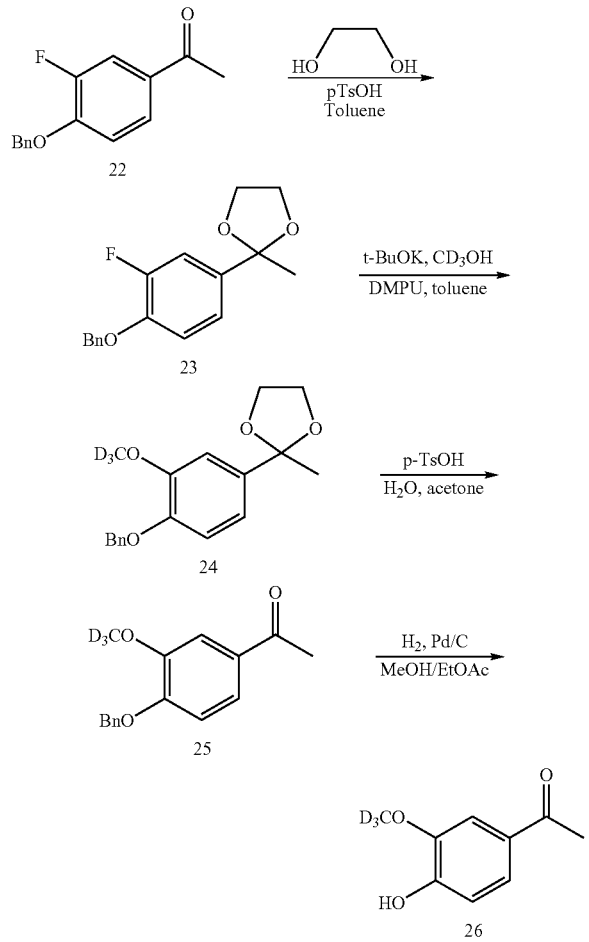

Synthesis of 2-(4-(benzyloxy)-3-fluorophenyl)-2-methyl-1,3-dioxolane (23)

A mixture of 1-(4-(benzyloxy)-3-fluorophenyl)ethanone 22 (23.8 g, 97.5 mmol), ethylene glycol (16.4 mL, 293 mmol), p-TsOH (930 mg, 4.88 mmol) and toluene (400 mL) was stirred under reflux conditions for 4 days, azeotropically removing water with a Dean-Stark trap. The mixture was cooled to room temperature and quenched by addition of saturated sodium bicarbonate solution (200 mL). The aqueous phase was back-extracted with toluene (3×200 mL). The combined organic phases were washed with brine (200 mL), dried over sodium sulfate, filtered and the solvent removed under reduced pressure to give 28.7 g (103%) of crude 23 as a yellow solid. Crude 23 was used without further purification. $^1$H NMR (CDCl$_3$) δ: 7.39 (m, 5H), 7.22 (dd, 1H), 7.16 (dd, 1H), 6.95 (t, 1H), 5.12 (s, 2H), 4.12 (dd, 2H), 3.77 (dd, 2H), 1.62 (s, 3H). LCMS m/z=289.1 (M+H).

Synthesis of 2-(4-(benzyloxy)-(3-methoxy-d3)phenyl)-2-methyl-1,3-dioxolane (24)

A mixture of potassium t-butoxide (24.8 g, 214.3 mmol), methanol-d$_3$ (11.8 mL, 299 mmol), 1,3-dimethyl-3,4,5,6-tetrahydro-2(1H)-pyrimidinone (17.6 mL) and toluene (44 mL) was heated at 100° C. for 0.5 hour (hr) to give a yellow suspension. Compound 23 (16.3 g, 56.4 mmol) was added and the mixture heated at 100° C. overnight. The mixture was cooled to room temperature, washed with water (200 mL) and 6N HCl (100 mL). The aqueous washings were combined and extracted with ethyl acetate (4×150 mL). The combined organic phases were washed with brine (100 mL), dried over sodium sulfate, and concentrated under reduced pressure to give 18 g of crude 24. Crude 24 was used directly for the next step without further purification. $^1$H NMR (CDCl$_3$) δ: 7.39 (m, 5H), 7.02 (d, 1H), 6.96 (d, 1H), 6.82 (d, 1H), 5.18 (s, 2H), 4.02 (dd, 2H), 3.78 (dd, 2H), 1.62 (s, 3H). LCMS m/z=304.1 (M+H).

Synthesis of 1-(4-(benzyloxy)-(3-methoxy-d3)phenyl)ethanone (25)

A mixture of crude 24 (18 g, 56.4 mmol) and p-TsOH (86 mg, 2.82 mmol) in acetone (150 mL) and a few milliliters of water was stirred at room temperature overnight. The solvent was removed under reduced pressure and the crude product that was purified by column chromatography using 0-100% ethyl acetate/hexanes to give 14 g (96%) of 25. $^1$H NMR (CDCl$_3$) δ: 7.40 (overlap, 7H), 6.92 (d, 1H), 5.22 (s, 2H), 2.57 (s, 3H). LCMS m/z=260.1 (M+H).

Synthesis of 1-(4-hydroxy-(3-methoxy-d3)phenyl)ethanone (26)

A mixture of 25 (14 g, 56 mmol)) and 20% Pd—C (700 mg, 5 wt %) in methanol (20 mL) and ethyl acetate (20 mL) was hydrogenated at 4 Bar H$_2$ for 2 hr. The mixture was filtered through a pad of Celite, washing the pad with ethyl acetate (200 mL). The filtrate solution was concentrated under reduced pressure and the crude product purified by column chromatography using 0-100% ethyl acetate/heptanes to give 2 g (22%) of 26. $^1$H NMR (CDCl$_3$) δ: 7.56 (m, 2H), 6.96 (d, 1H), 6.06 (s, 1H), 2.57 (s, 3H). LCMS m/z=170.1 (M+H).

Example 2

Synthesis of 1-(4-(3-(4-(6-fluorobenzo[d]isoxazol-3-yl)piperidin-1-yl)propoxy)-3-methoxy-d3-phenyl)ethanone (Compound 131)

The synthesis of compound 131 was carried as outlined in Scheme 5, below. Details of the synthesis are set forth below.

Scheme 5: Synthesis of Compound 131

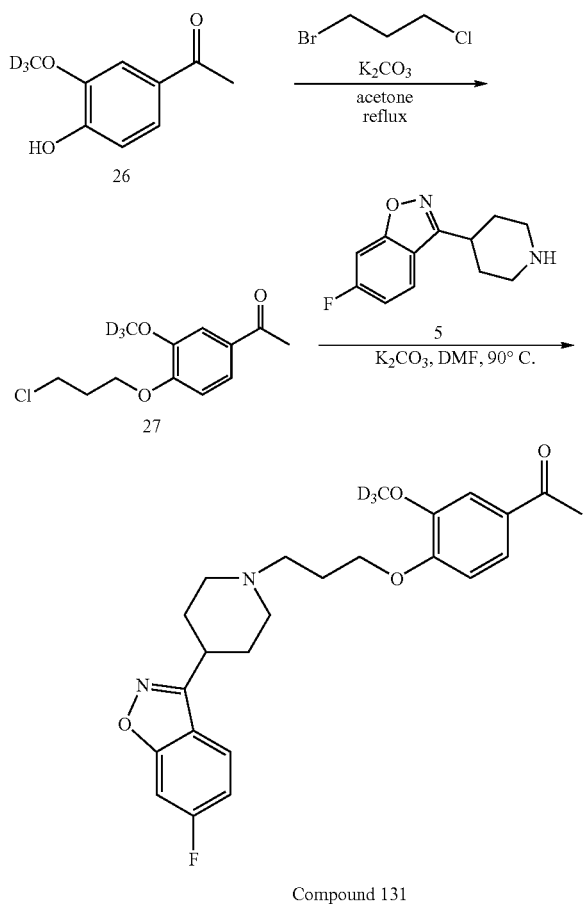

Compound 131

Synthesis of 1-(4-(3-chloropropoxy)-(3-methoxy-d3) phenyl)ethanone (27)

A mixture of 26 (1 g, 5.9 mmol), 1-bromo-3-chloropropane (1.2 mL, 11.8 mmol) and potassium carbonate (2.5 g, 17.7 mmol) in acetone (20 mL) was refluxed overnight. After cooling to room temperature, the solid was filtered and washed with acetone (100 mL). The filtrate was concentrated under reduced pressure and the crude product purified by column chromatography on silica gel using 1:1 heptanes/ethyl acetate to give 1.2 g (85%) of 27 as an oil that crystallized after standing overnight. $^1$H NMR (CDCl$_3$) δ: 7.56 (m, 2H), 6.92 (d, 1H), 4.23 (t, 2H), 3.76 (t, 2H), 2.58 (s, 3H), 2.34 (m, 2H). LCMS m/z=246.2 (M+H).

Synthesis of 1-(4-(3-(4-(6-fluorobenzo[d] isoxazol-3-yl)piperidin-1-yl)propoxy)-(3-methoxy-d3)phenyl) ethanone (Compound 131)

A mixture of 27 (0.68 g, 2.8 mmol), 6-fluoro-3-(piperidin-4-yl)benzo[d]isoxazole hydrochloride (5, 0.71 g, 2.8 mmol) and potassium carbonate (0.77 g, 5.6 mmol) in DMF (10 mL) was heated at ~90° C. overnight. After cooling to room temperature, the solid was filtered, washed with DMF (100 mL) and the filtrate was concentrated under reduced pressure. The crude product was purified by column chromatography on silica gel using 0-10% methanol/dichloromethane to give 750 mg (63%) of Compound 131 as a yellow solid. $^1$H NMR (CDCl$_3$) δ: 7.69 (q, 1H), 7.58 (m, 2H), 7.21 (m, 1H), 7.06 (m, 1H), 6.92 (d, 1H), 4.19 (t, 2H), 3.08 (m, 3H), 2.60 (t, 2H), 2.58 (s, 3H), 2.22-2.01 (overlap, 8H). HPLC (method: 20 mm C18-RP column—gradient method 2-95% ACN+0.1% formic acid in 3.3 min with 1.7 min hold at 95% ACN; Wavelength: 254 nm): retention time: 2.66 min. LCMS m/z=430.2 (M+H).

Example 3

Synthesis of 1-(4-(3-(4-(6-fluorobenzo[d]isoxazol-3-yl)piperidin-1-yl)propoxy-d6)-3-methoxy-d3-phenyl)ethanone (Compound 141)

Compound 141 was prepared in a similar manner to Scheme 5, above. Details of the synthesis are set forth below.

Synthesis of 1-(4-(3-bromopropoxy-d6)-(3-methoxy-d3)phenyl)ethanone (28)

A mixture of 26 (1 g, 5.9 mmol) and potassium carbonate (1.6 g, 11.8 mmol) in acetone (20 mL) was refluxed for 1.5 hr, then cooled to room temperature. Acetone was removed by concentration under reduced pressure to the crude potassium salt of 26 as a white powder. The crude salt was added in small portions over 4 hr to a refluxing solution of d6-dibromopropane (3.7 g. 17.7 mmol) in acetone (10 mL). After addition of the salt was complete, the reaction mixture was refluxed for 0.5 hr, then cooled to room temperature and stirred overnight. The product was isolated and purified by column chromatography on silica gel using 1:1 heptanes/ethyl acetate to give 1.2 g (68%) of 28 as a white solid. $^1$H NMR (CDCl$_3$) δ: 7.58 (m, 2H), 6.92 (d, 1H), 2.54 (s, 3H). LCMS m/z=296.0 (M+H).

Synthesis of 1-(4-(3-(4-(6-fluorobenzo[d] isoxazol-3-yl)piperidin-1-yl)propoxy-d6)-(3-methoxy-d3) phenyl)ethanone (Compound 141)

A mixture of 28 (0.82 g, 2.76 mmol), 6-fluoro-3-(piperidin-4-yl)benzo[d]isoxazole hydrochloride (5, 0.71 g, 2.76 mmol) and potassium carbonate (0.77 g, 5.6 mmol) in DMF (10 mL) was heated at 90° C. overnight. After cooling to room temperature, the solid was filtered and washed with DMF (100 mL). The filtrate was concentrated under reduced pressure and the crude product was purified by column chromatography on silica gel using 0-10% methanol/dichloromethane to give 650 mg (55%) of Compound 141 as a yellow solid. $^1$H NMR (CDCl$_3$) δ: 7.65 (q, 1H), 7.58 (m, 2H), 7.21 (m, 1H), 7.06 (m, 1H), 6.92 (d, 1H), 3.08 (m, 3H), 2.58 (s, 3H), 2.22-2.01 (overlap, 6H). LCMS m/z=436.2 (M+H).

Evaluation of Compound Stability

Certain in vitro liver metabolism studies have been described previously in the following references, each of which is incorporated herein in their entirety: Obach R S, Drug Metab. Disp. 1999, 27: 1350; Houston, J B et al., Drug Metab. Rev. 1997, 29: 891; Houston, J B Biochem Pharmacol 1994, 47: 1469; Iwatsubo T et al., Pharmacol. Ther. 1997, 73: 147; and Lave, T et al., Pharm. Res. 1997, 14: 152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.), or XenoTech, LLC (Lenexa, Kans.)). The incubation mixtures are prepared as follows:

| Reaction Mixture Composition | |
| --- | --- |
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (no test compound added). The reaction is initiated by the addition of cofactors (not added to the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as iloperidone, are each run simultaneously with the test compounds in separate reactions.

All samples are analyzed using LC-MS (or MS/MS). An LC-MRM-MS/MS method is used to examine metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Supersomes™ Assay. Various human cytochrome P450-specific Supersomes™, such CYP2D6 SUPERSOMES, are purchased from Gentest (Woburn, Mass., USA). A 1.0 mL reaction mixture containing 25 pmole of Supersomes™, 2.0 mM NADPH, 3.0 mM MgCl, and 1 µM of a compound of Formula I in 100 mM potassium phosphate buffer (pH 7.4) is incubated at 37° C. in triplicate. Positive controls contain 1 µM of Compound 1 instead of a compound of formula I. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:
1. A compound of Formula I

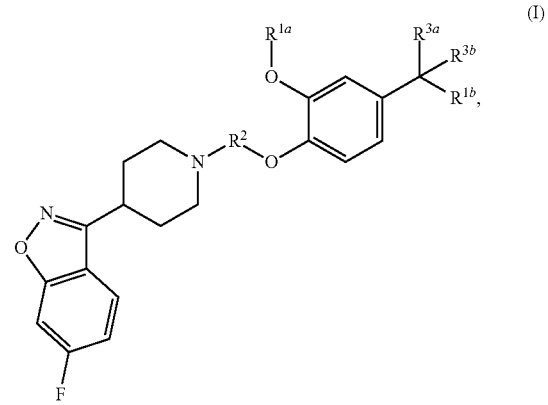

or a salt, hydrate, or solvate thereof, wherein:
each of $R^{1a}$ and $R^{1b}$ is -CD$_3$; or
$R^{1a}$ is CD$_3$ and $R^{1b}$ is CH$_3$;
$R^2$ is selected from CH$_2$CH$_2$CH$_2$, CD$_2$CD$_2$CD$_2$, CD$_2$CH$_2$CH$_2$, and CD$_2$CH$_2$CD$_2$;
a) $R^{3a}$ is selected from H, and D; and
$R^{3b}$ is —OH; or
b) $R^{3a}$ and $R^{3b}$ are simultaneously F; or
c) $R^{3a}$ and $R^{3b}$ are taken together, with the carbon atom to which they are bound, to form a carbonyl group; and
at least one of $R^{1a}$, $R^{1b}$, $R^2$, $R^{3a}$, and $R^{3b}$ comprises a deuterium atom, and wherein each atom designated as deuterium has a minimum isotopic enrichment factor of at least 3000 (45% deuterium incorporation).

2. The compound of claim 1, wherein $R^{1a}$ and $R^{1b}$ are simultaneously CD$_3$.

3. The compound of claim 1, wherein $R^{3a}$ and $R^{3b}$ are taken together with the carbon atom to which they are bound to form a carbonyl group.

4. The compound of claim 1, wherein $R^{3a}$ and $R^{3b}$ are simultaneously F.

5. The compound of claim 1, selected from any one of the compounds set forth in the following table:

| Cmpd | $R^{1a}$ | $R^{1b}$ | $R^2$ | $R^{3a}$ | $R^{3b}$ |
| --- | --- | --- | --- | --- | --- |
| 101 | CD$_3$ | CH$_3$ | CD$_2$CH$_2$CH$_2$ | H | OH |
| 104 | CD$_3$ | CH$_3$ | CD$_2$CH$_2$CD$_2$ | H | OH |
| 106 | CD$_3$ | CD$_3$ | CD$_2$CH$_2$CH$_2$ | H | OH |
| 107 | CD$_3$ | CD$_3$ | CD$_2$CH$_2$CD$_2$ | H | OH |
| 118 | CD$_3$ | CH$_3$ | CD$_2$CH$_2$CH$_2$ | F | F |
| 120 | CD$_3$ | CH$_3$ | CD$_2$CH$_2$CD$_2$ | F | F |
| 122 | CD$_3$ | CD$_3$ | CD$_2$CH$_2$CD$_2$ | F | F |
| 131 | CD$_3$ | CH$_3$ | CH$_2$CH$_2$CH$_2$ | =O | |
| 132 | CD$_3$ | CD$_3$ | CH$_2$CH$_2$CH$_2$ | =O | |

-continued

| Cmpd | R$^{1a}$ | R$^{1b}$ | R$^2$ | R$^{3a}$ | R$^{3b}$ |
|---|---|---|---|---|---|
| 134 | CD$_3$ | CH$_3$ | CD$_2$CH$_2$CH$_2$ | | =O |
| 136 | CD$_3$ | CD$_3$ | CD$_2$CH$_2$CH$_2$ | | =O |
| 138 | CD$_3$ | CH$_3$ | CD$_2$CH$_2$CD$_2$ | | =O |
| 140 | CD$_3$ | CD$_3$ | CD$_2$CH$_2$CD$_2$ | | =O |
| 141 | CD$_3$ | CH$_3$ | CD$_2$CD$_2$CD$_2$ | | =O |
| 142 | CD$_3$ | CH$_3$ | CD$_2$CD$_2$CD$_2$ | F | F |
| 143 | CD$_3$ | CH$_3$ | CH$_2$CH$_2$CH$_2$ | F | F |

6. The compound of claim 1, selected from:

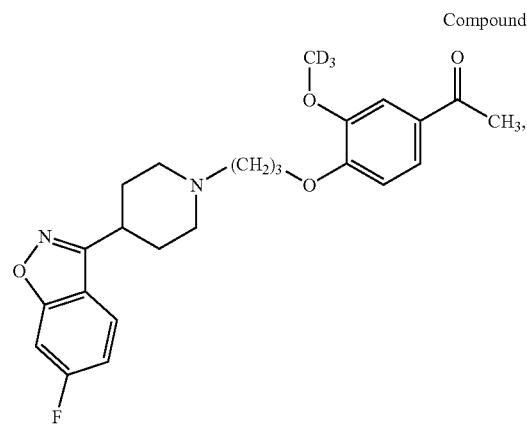

Compound 131

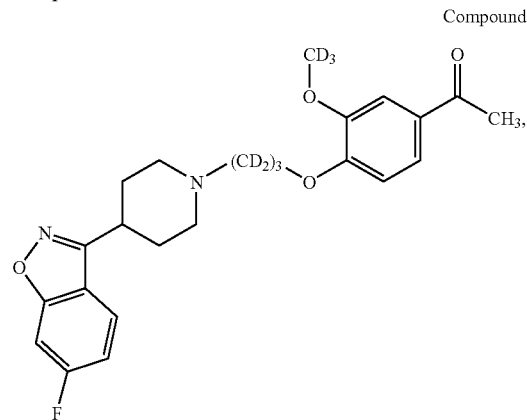

Compound 141

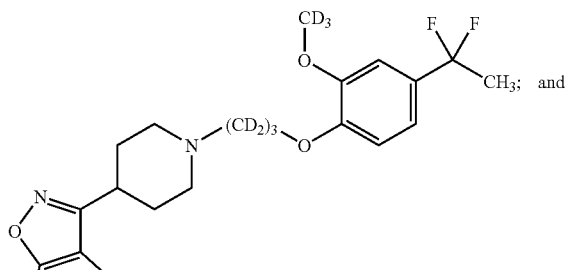

Compound 142

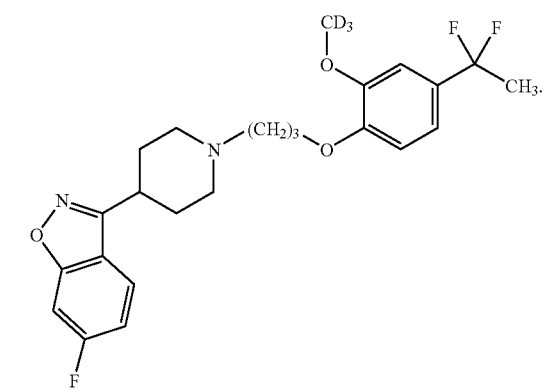

Compound 143

7. The compound of claim 1, wherein each atom not specified as deuterium is present at its natural isotopic abundance.

8. A pyrogen-free composition comprising an effective amount of the compound of claim 1 and an acceptable carrier.

9. The composition of claim 8, wherein said composition is formulated for pharmaceutical administration and the carrier is a pharmaceutically acceptable carrier.

\* \* \* \* \*